(12) United States Patent
Bellare et al.

(10) Patent No.: US 10,660,941 B2
(45) Date of Patent: May 26, 2020

(54) ORALLY ADMINISTRABLE PHARMACEUTICAL PREPARATION CONTAINING PROTEIN

(71) Applicant: INDIAN INSTITUTE OF TECHNOLOGY, BOMBAY, Mumbai (IN)

(72) Inventors: Jayesh Bellare, Mumbai (IN); Neelam Vishwanath Dwivedi, Mumbai (IN); Arunagirinathan Manickam Adhimoolam, Chennai (IN); Somesh Datt Sharma, Los Altos, CA (US)

(73) Assignee: INDIAN INSTITUTE OF TECHNOLOGY, BOMBAY, Mumbai (IN)

( * ) Notice: Subject to any disclaimer, the term of this patent is extended or adjusted under 35 U.S.C. 154(b) by 0 days.

(21) Appl. No.: 15/999,777

(22) PCT Filed: Feb. 17, 2017

(86) PCT No.: PCT/IN2017/000041
§ 371 (c)(1),
(2) Date: Aug. 20, 2018

(87) PCT Pub. No.: WO2017/141262
PCT Pub. Date: Aug. 24, 2017

(65) Prior Publication Data
US 2019/0290735 A1    Sep. 26, 2019

(30) Foreign Application Priority Data
Feb. 19, 2016 (IN) .............................. 201621005792

(51) Int. Cl.
*A61K 38/28* (2006.01)
*A61K 47/69* (2017.01)
(Continued)

(52) U.S. Cl.
CPC ............ *A61K 38/28* (2013.01); *A61K 9/0053* (2013.01); *A61K 9/5192* (2013.01);
(Continued)

(58) Field of Classification Search
CPC .... A61K 38/28; A61K 9/5192; A61K 9/0053; A61K 47/6923; A61K 47/542; A61K 47/6929
See application file for complete search history.

(56) References Cited

U.S. PATENT DOCUMENTS

| 5,955,096 A | 9/1999 | Santos et al. |
| 7,871,988 B1 | 1/2011 | Sung et al. |

(Continued)

FOREIGN PATENT DOCUMENTS

| CN | 102133190 A | 7/2011 |
| EP | 2254590 B1 | 10/2012 |

OTHER PUBLICATIONS

Delie et al, Polymeric Particulates to Improve Oral Bioavailability of Peptide Drugs, Molecules, 10(1): 65-80 (Year: 2005).*
(Continued)

*Primary Examiner* — Carlos A Azpuru
(74) *Attorney, Agent, or Firm* — Vorys, Sater, Seymour and Pease LLP

(57) ABSTRACT

An orally administrable pharmaceutical preparation containing a protein. More particularly, an orally administrable pharmaceutical preparation including a protein loaded on metal oxide nanoparticles and an amino acid; wherein the amino acid forms an adduct with the protein loaded on metal oxide nanoparticles. An process for the production of the afore-mentioned orally administrable pharmaceutical preparation is also disclosed.

18 Claims, 6 Drawing Sheets

(51) Int. Cl.
    *A61K 47/54*     (2017.01)
    *A61K 9/00*     (2006.01)
    *A61K 9/51*     (2006.01)

(52) U.S. Cl.
    CPC ........ *A61K 47/542* (2017.08); *A61K 47/6923* (2017.08); *A61K 47/6929* (2017.08)

(56) References Cited

U.S. PATENT DOCUMENTS

| | | | |
|---|---|---|---|
| 8,859,004 | B2 | 10/2014 | Zhang et al. |
| 2010/0166855 | A1 | 7/2010 | Sabetsky |
| 2013/0034602 | A1 | 2/2013 | Qian et al. |

OTHER PUBLICATIONS

Fonte et al, Oral Insulin Delivery: How Far Are We., J Diabetes Sci Tecnolo, 7(2): 520-531 (Year: 2012).*

Florence Delie et al., "Polymeric Particulates to Improve Oral Bioavailability of Peptide Drugs", Molecules, Jan. 31, 2005, vol. 10, No. 1, pp. 65-80, XP055409897 [Y] 1-18, Introduction Para 030.

Pedro Fonte et al., "Oral Insulin Delivery: How Far Are We?", J Diabetes Sci Technol, (20130300), vol. 7, No. 2, pp. 520-531, XP055409898 [Y] 1-18, Abstract para 002 line 1-6, Introduction p. 525 last para line 1-3.

Ken-Tye Yong et al., "Preparation of Quantum Dot/Drug Nanoparticle Formulations for Traceable Targeted Delivery and Therapy", Theranostics, (2012), vol. 2, No. 7, pp. 681-694, XP055409900 [Y] 1-18, Introduction para 006 & fig 3.

International Search Report and Written Opinion dated Apr. 27, 2017 for PCT/IN2017/000041 to Indian Institute of Technology, Bombay filed Feb. 17, 2017.

C. I. Olariu et al., "Inorganic—Organic Hybrid Nanoparticles for Medical Applications", Jul. 7, 2010, Adv Struct Mater (2013) 4:8 5-133.

* cited by examiner

ORALLY ADMINISTRABLE PHARMACEUTICAL PREPARATION CONTAINING PROTEIN

CROSS-REFERENCE TO RELATED APPLICATIONS

This is a § 371 National Stage Application of International Application No. PCT/IN2017/000041 filed on Feb. 17, 2017, claiming the priority of Indian Patent Application No. 201621005792 filed on Feb. 19, 2016.

FIELD OF THE INVENTION

The present invention relates to an orally administrable pharmaceutical preparation containing a protein. More particularly, the present invention relates to an orally administrable pharmaceutical preparation comprising a protein loaded on metal oxide nanoparticles and an amino acid; wherein the amino acid forms an adduct with the protein loaded on metal oxide nanoparticles. The present invention relates to a process for the production of the afore-mentioned orally administrable pharmaceutical preparation as well.

BACKGROUND OF THE INVENTION

Diabetes is characterized by abnormally high levels of the sugar glucose in the bloodstream. Complications include blindness, kidney failure, heart disease, stroke, neuropathy, and amputations. Type-1 diabetes typically affects children and young adults. It occurs when the islet cells of the pancreas are destroyed and stop producing insulin. Insulin deficiency causes a disease called diabetes mellitus and, hence, administration of exogenous insulin is used to control this disease. It has been recorded by "International Diabetes Federation" in November 2014 that 387 million people have diabetes in the world and it caused 4.9 million deaths in 2014. The global health expenditure in diabetes estimated to be $612 billion. India has more diabetic patients than any other country with 32.7 millions of cases.

One of the biggest obstacles in type-1 diabetes is to deliver insulin 3-4 times in a day by injection and till date injections are the only efficient way to deliver insulin with maximum bioavailability in market. Insulin therapy has been around for 80 years, yet alternative methods of insulin delivery have been slow to emerge. The reason for this is that acids and enzymes present in stomach and intestines easily break down the protein insulin or if the technology gets succeeded then it results in very low bioavailability of the protein. Insulin promotes the entry of glucose, fatty acids and amino acids into cells and enhances glycogen, protein and lipid synthesis. Insulin is made up of two polypeptide chains namely, chain-A (21 amino acids) and chain-B (30 amino acids), which are held together by two disulfide bonds. Insulin exists as a monomer, dimer or hexamer. Each hexamer binds to $Zn^{+2}$ ions which co-ordinates crystal formation within β granules. Molecular weight of insulin is 5500 dalton.

The various preparations of insulin available in the market include bovine insulin (from cattle), porcine insulin (from pig, a mixture of both, or recombinant human insulin. Since insulin has a very short life in the plasma, insulin products that last longer are also available. In these products, insulin is complexed with zinc, globin, protamine or a combination of any of these. These insulin preparations are required to be given through an injection which is very painful to take daily and also do not result in adequate reduction of glucose levels after meal. Hence, they are often given to the subject along with other anti-diabetes drugs.

Alternate routes of delivery for insulin like oral-buccal route, pulmonary route (lung alveoli), nasal delivery, transdermal, rectal and ocular have been a topic of intense R&D to improve. Among all, the oral route offers maximum advantage, from both physicians as well as patient perspectives.

Macromolecules like insulin exhibit structural and functional variations and are integral to the regulation and maintenance of all biological processes. The increased biochemical and structural complexity of insulin compared to conventional drug-based pharmaceuticals makes formulation design for oral delivery of therapeutic insulin is a very challenging and difficult task. The key to success of macromolecules like insulin as pharmaceuticals is to have in place an efficient drug delivery system that allows the drugs to gain access to their target sites at right time for proper duration.

The various oral preparations for delivery of protein macromolecules disclosed in the prior art are as follows:

1) CN102133190A—This patent application discloses transferrin protein nanoparticles for delivering drugs such as insulin. The formulation is going under high pressure homogenization to obtain insulin linked transferrin nanoparticles (approx. 250 nm). A drawback of this patent application is that the extraction of transferrin is difficult as well as high amount of transferrin (100 mg) is needed for 10-15 mg of insulin. The insulin has to undergo high pressure homogenization to link with transferrin. The formulation is showing only 20% reduction in blood glucose level. For scale-up, this formulation will be difficult to work out as well as it will be costly, since there will be more degradation of insulin protein due to homogenization process.

2) U.S. Pat. No. 7,871,988—This patent uses using chitosan and polyglutamic acid for the insulin system. Chitosan is having cationic charge and it helps in paracellular permeability of the formulation. The formulation is tested in diabetic rats and it is able to reduce 30% glucose level in 3 hours while the freeze dried formulation is not able to reduce glucose. Synthesizing chitosan is itself complex and its molecular weight varies due to which large scale production will be difficult and the particle size will not be controlled too.

3) U.S. Pat. No. 8,859,004—This patent discloses a formulation which is pH based and releases insulin from formulation at neutral pH. It consists of two polymers like PLGA and HP50/HP55 and the formulation is made by solvent evaporation step and freeze drying. The formulation is not suitable for large scale manufacturing due to the presence of residual organic solvent and it will be costly as well.

4) US20100166855—This patent application discloses a two phase system made up of dextran microparticles which are formed by solvent evaporation method. This is a costly process as well as during scale-up it may face the problem of residual organic solvent in final formulation. The formulation reduces 30% glucoses in 1 hour.

5) US20130034602—This patent application discloses a complex formulation due to double emulsions (PLGA and Eudragit RS) as well as insulin is exposed to organic solvent (polyvinyl alcohol) while encapsulation. The formulation disclosed in the patent application will be difficult to scale-up as well as not affordable and it will face problem of residual organic solvent. The formulation results in 30% reduction of glucose levels in around 7 hours.

The present invention provides an orally administrable pharmaceutical preparation containing a protein such as insulin by using metal oxide nanoparticles and an amino acid which provides a charge based system to allow easy engulfment of the protein preparation though the epithelial cells or the Peyer's patches in the gut line.

SUMMARY OF THE INVENTION

In one aspect, the present invention provides an orally administrable pharmaceutical preparation comprising a protein loaded on metal oxide nanoparticles and an amino acid; wherein the amino acid forms an adduct with the protein loaded on metal oxide nanoparticles.

In another aspect, the present invention provides a process for the production of orally administrable pharmaceutical preparation comprising the steps of:
  a. synthesizing metal oxide nanoparticles by hydrolysis of metal salts and storing the nanoparticles suspension at 0° C. to 10° C.;
  b. dissolving a protein in an aqueous solution and adjusting the pH of the solution from 7 to 2 pH;
  c. adding the protein solution of step (b) to the nanoparticles suspension of step (a);
  d. mixing an amino acid solution with a carbodiimide (CDI) solution for 1 minute to 120 minutes and adjusting the pH of the resultant solution to 8 to 9 using an acid;
  e. adding the amino acid-CDI mixture of step (d) to the suspension of step (c) and maintaining the pH of the solution at the isoelectric point of the protein and storing the resultant solution at 0° C. to 10° C. for 12 hours to 48 hours; and
  f. washing the settled nanoparticles with an aqueous solution to obtain the orally administrable pharmaceutical preparation containing protein.

Advantages of the Present Invention

Rapid absorption in the gastrointestinal tract due to nano-suspension.
Controlled release of proteins such as insulin.
The orally administrable pharmaceutical preparation containing the protein insulin is pharmacodynamic equivalent to the subcutaneous insulin.
The orally administrable pharmaceutical preparation of the present invention is absorbed via receptor mediated endocytosis and is tolerant to the gastric pH and enzymes of the body.
The orally administrable pharmaceutical preparation of the present invention is in suspension state which can be easily given to adults and children.
Stability: Bioactivity of the protein insulin is seen in 15 days old freeze dried formulation as well as in the suspension state preparation.

BRIEF DESCRIPTION OF THE DRAWINGS

The foregoing summary, as well as the following detailed description of the invention will be better understood when read in conjunction with the appended drawings. For the purpose of assisting in the explanation of the invention, there are shown in the drawings embodiments which are presently preferred and considered illustrative. It should be understood, however, that the invention is not limited to the precise arrangements and instrumentalities shown therein.

DESCRIPTION OF THE INVENTION

Figure 1:
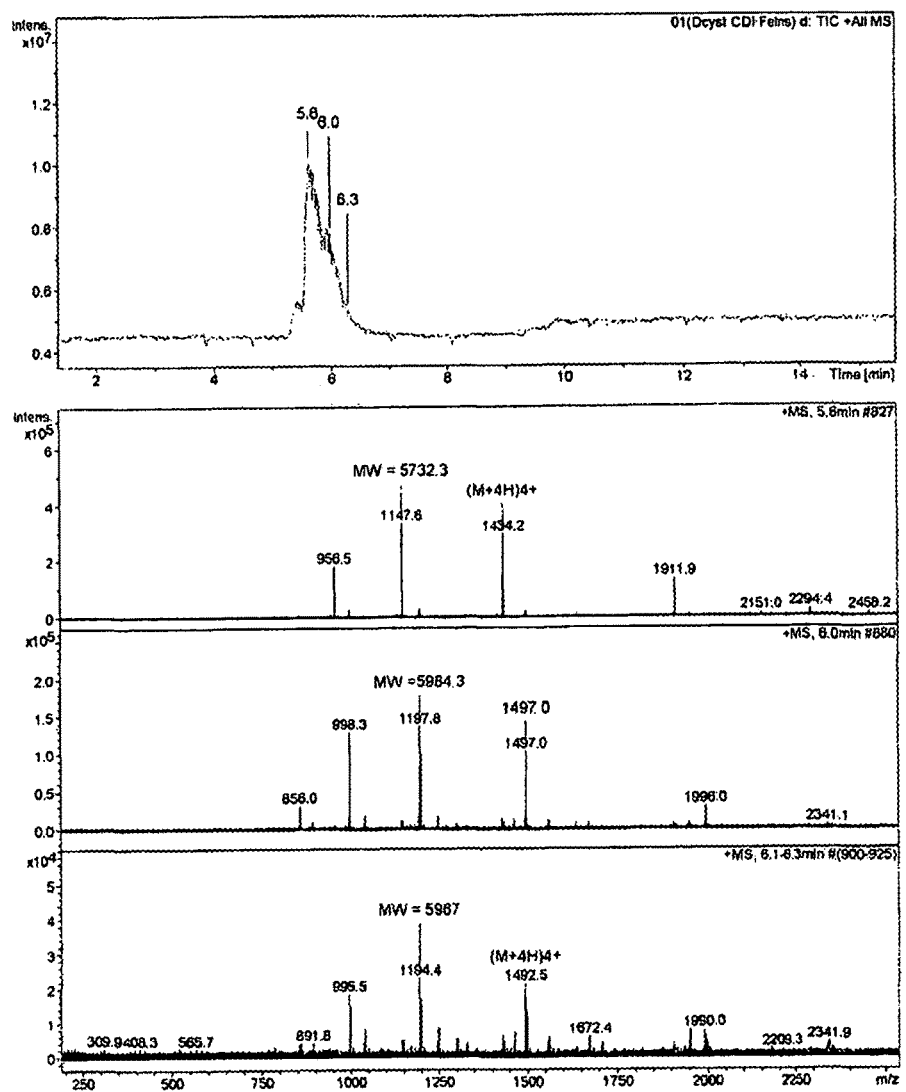
FIG. 1: Mass spectrometry confirms formulation contains free insulin (m/z: 5732) and d-cystine/insulin adducts (m/z: 5984, 5967).

In describing the invention, the following terminology will be used in accordance with the definitions set forth below. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section. Specific and preferred values listed below for individual process parameters, substituents, and ranges are for illustration only; they do not exclude other defined values or other values falling within the preferred defined ranges. All publications mentioned herein are incorporated by reference to disclose and describe the methods and/or materials in connection with which the publications are cited.

As used herein, the singular forms "a," "an," and "the" include plural reference unless the context clearly dictates otherwise.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

When the term "about" is used in describing a value or an endpoint of a range, the disclosure should be understood to include both the specific value or end-point referred to.

As used herein, the terms "comprises", "comprising", "includes", "including", "containing", "characterized by", "having" or any other variation thereof, are intended to cover a non-exclusive inclusion.

As used herein, the term "isoelectric point" refers to the pH value where the overall net charge of a macromolecule such as a protein is zero. In proteins there may be many charged groups, and at the isoelectric point the sum of all these charges is zero, i.e. the number of negative charges balances the number of positive charges. At a pH above the isoelectric point the overall net charge of the protein will be negative, whereas at pH values below the isoelectric point the overall net charge of the protein will be positive.

In one aspect, the present invention provides an orally administrable pharmaceutical preparation comprising a protein loaded on metal oxide nanoparticles and an amino acid; wherein the amino acid forms an adduct with the protein loaded on metal oxide nanoparticles.

The proteins used in the pharmaceutical preparation of the present invention are the proteins which are stable at lower pH 1-3 and its isoelectric point is 4 to 6. Non limiting examples of the protein include insulin, insulin analog, insulin derivative, insulin growth factor, GLP-1, calcitonin, interferon, human growth hormone, glucagon, gonadotropin-releasing hormone, glycoprotein, cytokine, interleukin, vaccine, enzyme, hormone analog, an antibody, a $F_{ab}$ Fragment, trypsin, enfuvertide, pramlintide acetate or enzyme inhibitors.

In a most preferred embodiment of the present invention, the protein is insulin which may be selected from the group consisting of porcine insulin, bovine insulin, feline insulin, human insulin, recombinant insulin, lispro insulin, humalog, lantus, levemir, actrapid, novorapid, velosulin, humulin M3, hypurin, insuman, insulatard, mixtard, aspart insulin, glargine insulin, insulin glulisine, isophane insulin, insulin detemir, insulin zinc extended, novolin R, humulin R, humulin R regular U-500, novolin N, Humulin N, ReliOn, afrezza, humulin 70/30, novolin 70/30, novolog 70/30, humulin 50/50, humalog mix 75/25.

The metal oxide nanoparticles are selected from the group consisting of iron oxide, aluminium hydroxide, magnesium hydroxide, alumina, aluminosilicate, aluminosilicophosphate, silica, zinc oxide, titania, zirconia, tantalum oxide.

The final product i.e. the adduct of the amino acid with the protein loaded on metal oxide nanoparticles has a size less than 500 nm whereas the metal oxide nanoparticles have a size in the range of 3-5 nm.

The amino acid is a sulfur containing amino acid; preferably the amino acid is d-cystine. The amino acid is linked to the protein coated or loaded on metal oxide nanoparticles via carbodiimide linkage.

Figure 5:
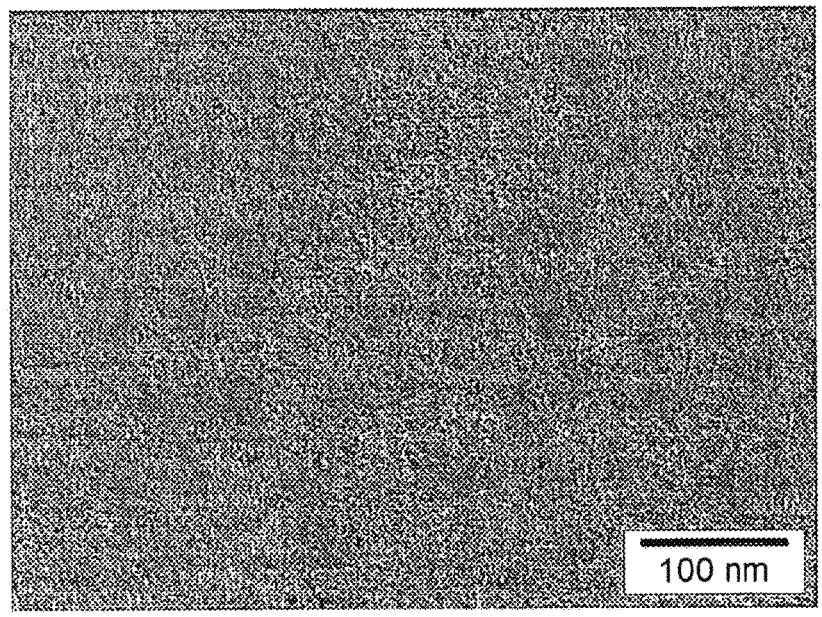
FIG. 5: TEM image of ferrite nanoparticles Bar=100 nm.

The orally administrable pharmaceutical preparation of the present invention is an adduct wherein the protein is adsorbed on the metal oxide nanoparticles and the amino acid encapsulates the protein loaded on metal oxide nanoparticles at the isoelectric point of the protein. Preferably, the orally administrable pharmaceutical preparation of the present invention is adduct of d-cystine linked with insulin coated α-iron oxide nanoparticles. Discrete ferrite nanoparticles 3-5 nm (FIG. 5) present in solution aggregated on adding insulin which indicated that the surface hydroxyl groups present on ferrite nanoparticles favors insulin adsorption. Indeed, the ten times excess ferrite (5.5 mM) present in solution has stabilized the insulin-ferrite aggregates to remain in suspension. During later stage, to form adducts with d-cystine, insulin coated on ferrite nanoparticles exposes it active sites for effective conjugation, although the active sites are not identified here. Carbodiimide activator present in reaction mixture also enhances binding of ferrite with proteins and conjugation of protein with d-cystine due to reaction between hydroxyl, carboxyl and amino groups present in the reacting mixture constituents. As d-cystine is very stable to gastric fluids, it has formed protective shell around the insulin-ferrite aggregates and prevented the degradation of insulin from gastric environment during oral administration.

As the protein such as insulin macromolecules are adsorbed above ferrite nanoparticle, it has favorably exposed the active sites for adduct formation. Synergistically, the d-cystine present in the adduct protected the formulation from gastric environment and facilitated absorption through rBAT/b0,+ AT cystine transporter and other transporters present in the gut line, kidney, liver and X_C transporter present in pancreatic islet cells thereby reducing glucose blood sugar level efficiently. d-cystine was used for insulin delivery since it is biocompatible, has excellent physical, chemical stability and entraps polycationic insulin in d-cystine by polymerizing with carbodiimide. Also, tagging of d-cystine (pH8) to Fe-Insulin (pH 1) occurs due to opposite charges. Thus encapsulation of insulin is taking place within d-cystine between pH 5 to 5.5. d-cystine coating helps the formulation from gastric pH and enzyme, while tagging insulin with ferrite nanoparticles is enhancing the engulfment through epithelial cells (ferritin receptors in gut) or Peyer's patches in gut line via receptor-mediated endocytosis.

The orally administrable pharmaceutical preparation of the present invention is stable, inexpensive, biocompatible and depending on size reaches different body organs. The ferrite nanoparticles also facilitate absorption through gut line via D-cytochrome B (Dcyt B) or divalent metal transporter 1 (DMT1) or ferritin receptors. Before administrating to animals orally, ferrite nanoparticles in a suspension state is added to the formulation so that rapid absorption of insulin is taking place from gut line and within an hour reduction in plasma glucose level is observed in Wistar rats.

In another aspect, the present invention also provides a process for the production of orally administrable pharmaceutical preparation comprising the steps of:
  a. synthesizing metal oxide nanoparticles by hydrolysis of metal salts and storing the nanoparticles suspension at 0° C. to 10° C.;
  b. dissolving a protein in an aqueous solution and adjusting the pH of the solution from 7 to 2 pH;
  c. adding the protein solution of step (b) to the nanoparticles suspension of step (a);
  d. mixing an amino acid solution with a carbodiimide (CDI) solution for 1 minute to 120 minutes and adjusting the pH of the resultant solution to 8 to 9 using an acid;
  e. adding the amino acid-CDI mixture of step (d) to the suspension of step (c) and maintaining the pH of the solution at isoelectric point of the protein and storing the resultant solution at 0° C. to 10° C. for 12 hours to 48 hours; and
  f. washing the settled nanoparticles with an aqueous solution to obtain the orally administrable pharmaceutical preparation containing protein.

In a preferred embodiment of the present invention, the metal oxide nanoparticles is α-iron oxide nanoparticles, the protein is insulin, the amino acid is d-cystine and the pH of the pharmaceutical preparation is 5.5. Also, the pharmaceutical preparation prior to administration is suspended in the aqueous solution and metal oxide nanoparticle suspension and the pH is maintained at 1 to 2.5.

In an embodiment of the present invention, the amino acid solution is prepared by dissolving the amino acid in a basic solution; wherein the basic solution is 30% ammonium hydroxide in distilled water.

The carbodiimide (CDI) solution is prepared by dissolving carbodiimide in the aqueous solution and the aqueous solution is selected from the group consisting of water, distilled water, double distilled water or sterilized water.

The following examples are provided to better illustrate the present invention and are not to be interpreted in any way as limiting the scope of the invention. All specific materials and methods described below, in whole or in part, fall within the scope of the invention. These specific compositions, materials, and methods are not intended to limit the invention, but merely to illustrate specific embodiments falling within the scope of the invention. One skilled in the art may develop equivalent materials, and methods without the exercise of inventive capacity and without departing from the scope of the invention. It will be understood that many variations can be made in the procedures herein described while still remaining within the bounds of the invention. It is the intention of the inventors that such variations are included within the scope of the invention.

EXAMPLES

1) Materials d-cystine, N-Cyclohexyl-N'-(2-morpholinoethyl) carbodiimidemetho-p-toluenesulfonate and bovine insulin from Sigma-Aldrich, HCl and Ammonia of analytical grade from local suppliers were used as obtained.

2) Formulations

Formulation 1: Protocol to Synthesize d-cystine-CDI-Fe-Insulin Formulation $\alpha$-$Fe_2O_3$ nanoparticles (3-5 nm particle size, pH 1) were synthesized by hydrolysis of $FeCl_3$ in boiling water and stored at 4° C. (N. J. Cherepy, D. B. Liston, J. A. Lovejoy, H. Deng, J. Z. Zhang. *J. Phys. Chem. B*, 102, 770 (1998)). A 2.5 ml of $\alpha$-$Fe_2O_3$ suspension (825.3 ppm) was taken in a glass bottle. 15 mg of insulin powder was dissolved in separate eppendorf by adding 2 ml D/W [1.99 ml D/W+100 µl of 0.05M HCl (pH 2)]. Insulin solution was added to the vial containing $\alpha$-$Fe_2O_3$ nanoparticles suspension. 15 mg of d-cystine was dissolved in separate vial using 100 µl of 30% ammonium hydroxide in 1 ml D/W. 30 mg of carbodiimide (CDI) was taken in a separate vial and dissolved using 1 ml D/W. d-cystine and CDI was mixed and kept for 5 minutes to activate $COO^-$ group.

The pH of d-cystine-CDI mixture was decreased to 8-8.5 using 0.05M HCl. Slowly d-cystine-CDI mixture (4 ml=Total volume) was added to $\alpha$-$Fe_2O_3$-insulin suspension and pH was maintained at 5.5, later stored at 4° C. for 24 hr. Next day, the settled nanoparticles were washed with D/W to remove excess CDI and stored for further studies. For in vivo study, the formulation was suspended in 0.250 ml D/W and 0.5 ml of $\alpha$-$Fe_2O_3$ suspension (total volume=2 ml).

Stability study at freeze dried powder state and suspension state is studied in 4 hr fasted normal Wistar rats. Freeze dried powder was made by using Christ $\alpha$ 1-2 CO Plus, Freeze drying Instrument. Time=12 hrs. Ice condenser=−60° C., Vacuum=0.001 mbar, Vacuum mbar=>−76° C.

Formulation 2: Protocol to Synthesize d-glutamine-CDI-Fe-Insulin (Without d-cystine)

Synthesize $\alpha$-$Fe_2O_3$ nanoparticles (3-5 nm particle size, pH 1) by hydrolysis method. Store at 4° C. A 2.5 ml of $\alpha$-$Fe_2O_3$ suspension (825.3 ppm) was taken in a glass bottle. 15 mg of insulin powder was dissolved in separate eppendorf by adding 2 ml D/W [1.99 ml D/W+100 µl of 0.05M HCl (pH 2)]. Insulin solution was added to the vial containing $\alpha$-$Fe_2O_3$ nanoparticles suspension. 15 mg of d-glutamine was dissolved in separate vial using 100 µl of 30% ammonium hydroxide in 1 ml D/W. 30 mg of carbodiimide (CDI) was taken in a separate vial and dissolved using 1 ml D/W. D-glutamine and CDI was mixed and kept for 5 minutes to activate $COO^-$ group.

The pH of d-glutamine-CDI mixture was decreased to 8-8.5 using 0.05M HCl. Slowly d-glutamine-CDI mixture (4 ml=Total volume) was added to $\alpha$-$Fe_2O_3$-insulin suspension and pH was maintained at 5.5, later stored at 4° C. for 24 hr. Next day, the settled nanoparticles were washed with D/W to remove excess CDI and stored for further studies. For in vivo study, the formulation was suspended in 0.250 ml D/W and 0.5 ml of $\alpha$-$Fe_2O_3$ suspension (total volume=2 ml).

Formulation 3: Protocol to Synthesize d-cystine-Insulin (Without CDI and Ferrite)

15 mg of insulin powder was dissolved in separate eppendorf by adding 2 ml D/W [1.99 ml D/W+100 µl of 0.05M HCl (pH 2)]. 15 mg of d-cystine was dissolved in separate vial using 100 µl of 30% ammonium hydroxide in 1 ml D/W. The pH of d-cystine was decreased to 8-8.5 using 0.05M HCl. Slowly d-cystine (4 ml=Total volume) was added to insulin suspension and pH was maintained at 5.5, later stored at 4° C. for 24 hr. Next day, the settled nanoparticles were washed with D/W to remove excess CDI and stored for further studies. For in vivo study, the formulation was suspended in 1 ml of D/W containing 100 microlitre of 0.05M HCl (total volume=2 ml).

Formulation 4: Protocol to Synthesize d-cystine-CDI-Insulin (Without Ferrite)

15 mg of insulin powder was dissolved in separate eppendorf by adding 2 ml D/W [1.99 ml D/W+100 µl of 0.05M HCl (pH 2)]. Insulin solution was added to the vial. 15 mg of d-cystine was dissolved in separate vial using 100 µl of 30% ammonium hydroxide in 1 ml D/W. 30 mg of carbodiimide (CDI) was taken in a separate vial and dissolved using 1 ml D/W. d-cystine and CDI was mixed and kept for 5 minutes to activate $COO^-$ group.

The pH of d-cystine-CDI mixture was decreased to 8-8.5 using 0.05M HCl. Slowly d-cystine-CDI mixture (4 ml=Total volume) was added to insulin suspension and pH was maintained at 5.5, later stored at 4° C. for 24 hr. Next day, the settled nanoparticles were washed with D/W to remove excess CDI and stored for further studies. For in vivo study, the formulation was suspended in 1 ml of D/W containing 100 microlitre of 0.05M HCl (total volume=2 ml).

Formulation 5: Protocol to Synthesize Fe-Insulin (Without d-cystine-CDI)

$\alpha$-$Fe_2O_3$ nanoparticles (3-5 nm particle size, pH 1) were synthesized by hydrolysis of FeCl3 in boiling water and stored at 4° C. (N. J. Cherepy, D. B. Liston, J. A. Lovejoy, H. Deng, J. Z. Zhang. *J. Phys. Chem. B*, 102, 770 (1998)). A 2.5 ml of $\alpha$-$Fe_2O_3$ suspension (825.3 ppm) was taken in a glass bottle. 15 mg of insulin powder was dissolved in separate eppendorf by adding 2 ml D/W [1.99 ml D/W+100 µl of 0.05M HCl (pH 2)]. Insulin solution was added to the vial containing $\alpha$-$Fe_2O_3$ nanoparticles suspension. The pH of ferrite-insulin was maintained at 5.5, later stored at 4° C. for 24 hr. Next day, the settled nanoparticles were washed with D/W and stored for further studies. For in vivo study, the formulation was suspended in 0.250 ml D/W and 0.5 ml of $\alpha$-$Fe_2O_3$ suspension (total volume=2 ml).

3) Characterization of Formulation

Confocal Microscopy:

Fluorophore tagged insulin (FITC-insulin) containing formulations were observed on glass cover slips under Confocal Laser Scanning Microscope (Fluoview FV500, Olympus) using Multi Argon Laser, 488 nm.

TEM:

The drop of the formulation in a suspended state was applied on carbon coated TEM grid, allowed to dry and later observed under TEM (Tecnai T-12, FEI).

HPLC:

Insulin content of the samples was analyzed using HPLC-UV at 270 nm (Waters, Photo diode array detector). Gradient elution was performed using 100% acetonitrile and 0.1% TFA at a flow-rate of 1 ml/min and injection volume of 20 µl. Insulin was detected at a retention time of 5.7 min with detection limit of 0.01 mg/ml.

FTIR:

The samples were mixed with KBr and compressed into discs at 20 kN force at room temperature. Bovine insulin powder, freeze dried formulation and d-cystine were analyzed by FTIR (Magna 550, Nicolet Instruments Corporation, USA).

SGF AND SIF Study:

50 mg formulation containing 0.45 mg of insulin were added separately to 2 ml of simulated gastric fluid (SGF) and simulated intestinal fluid (SIF) in triplicate and studied at 37° C. in shaking mode. 100 µl of the sample was withdrawn at definite interval and reaction was arrested by adding chilled 100 µl acetonitrile. The amount of insulin released over a period of 60 min in SGF and SIF was determined using HPLC.

Biological Activity of Formulation:

The biological activity of the insulin encapsulated in formulation was tested in a rat model (Wistar rats, 200+/−25 g, n=3) by measuring decrease in blood glucose levels. Animals fasted (4 hr) were anesthetized with isoflurane. Experimental animals received a subcutaneous injection of bovine insulin (2 IU/Kg) while the control animals with distilled water and test animals with varying doses of insulin encapsulated in desired formulations. Blood samples were withdrawn at 0, 15, 30, 60, 120, 240 min after subcutaneous injection. Blood samples were then centrifuged at 4° C., 7000 rpm to separate plasma from red blood cells. A 30 µl of plasma was mixed with 150 µL of saline and vortexed for few seconds and subjected to in situ glucose oxidase method in Hitachi 902, glucose analyzer. The results were expressed as the mean+/−S.E.

4) Results

Ferrite is used in the formulation to adsorb insulin in molecular state and into nanoparticle form, biocompatible as well as depending on size reaches different body organs. D-cystine was used for insulin delivery since it is biocompatible, inexpensive, excellent physical & chemical stability, controlled and room temperature production possible. Entrapment of insulin in d-cystine by polymerising with CDI helps in formation of peptide bond between amino acids by dehydrating the system and CDI is easily removed by washing with D/W. Before giving to animals it is dissolved with help of acidic ferrite solution/HCl. This insulin containing suspension has web like structures as observed under TEM.

Figure 2:
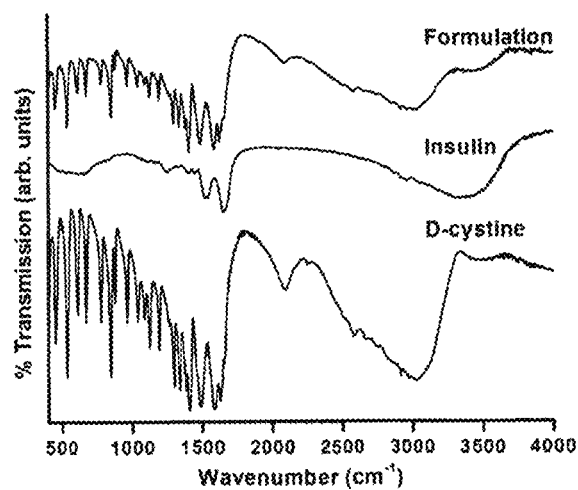
FIG. 2: FTIR of formulation compared with bovine insulin and d-cystine.
Figure 3:
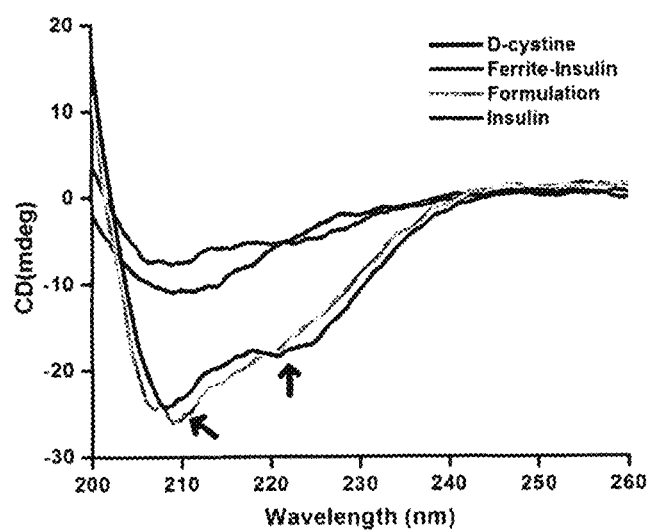
FIG. 3: Circular dichroism of formulation with bands at 208 nm and 222 nm indicate alpha helical secondary structure of insulin.
Figure 4:
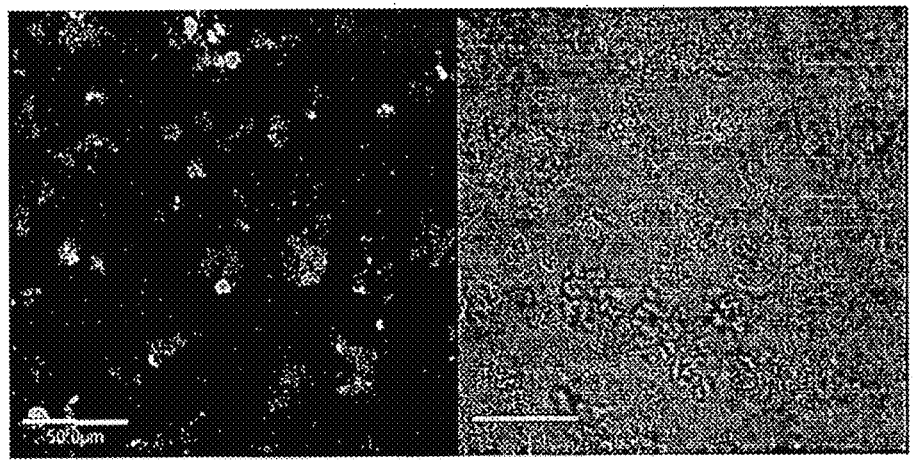
FIG. 4: Confocal microscopy of formulation. FITC-Insulin entrapped in the aggregated structure is observed under confocal mode, Bar=50μ.
Figure 6:
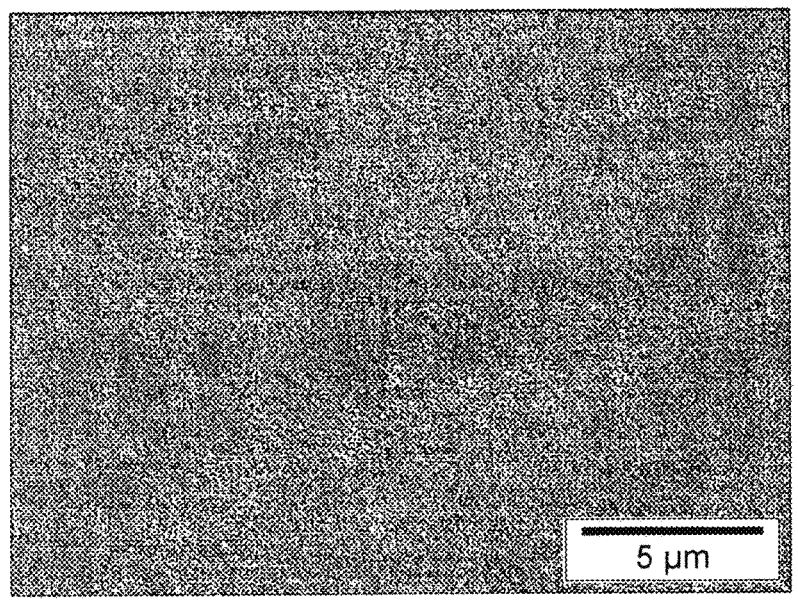
FIG. 6: TEM image shows sheath morphology of formulation Bar=5μ.

LC-MS spectra of formulation having signatures at m/z: 5732 (insulin); and m/z: 5967, 5984 (insulin-d-cystine adducts) (FIG. 1) indicate conjugation of d-cystine with insulin and FTIR spectroscopy revealing S—S stretching (540 cm$^{-1}$) and C—S stretching (675 cm$^{-1}$) (FIG. 2) indicate stability of insulin. The ferrite nanoparticles around 3-5 nm is evident from TEM (FIG. 5) and the final formulation is having aggregated structures which contains ferrite nanoparticles (FIG. 6). Confocal microscopy (FIG. 4) confirms formation of insulin-ferrite-d-cystine aggregates which encapsulates ~90% of total insulin as determined from HPLC. Circular dichroism at different stages of formulation preparation exhibited bands at 208 nm and 222 nm (FIG. 3) implying preservation of alpha helical secondary structure of insulin throughout the process.

Figure 7:
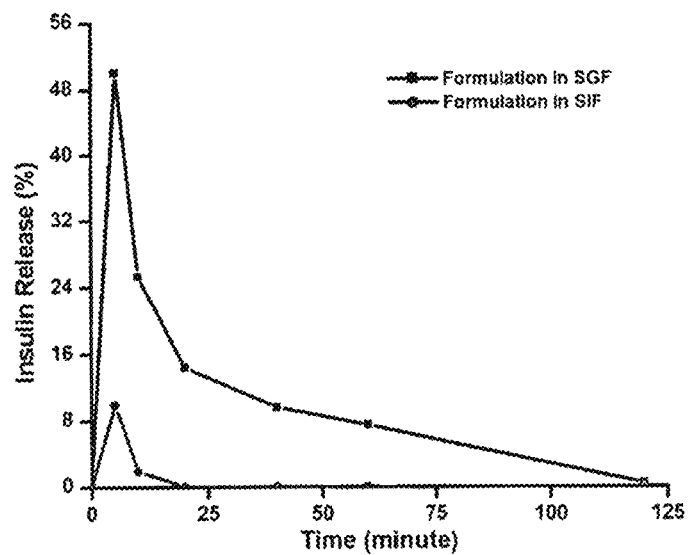
FIG. 7: SGF/SIF study of formulation.
Figure 8:
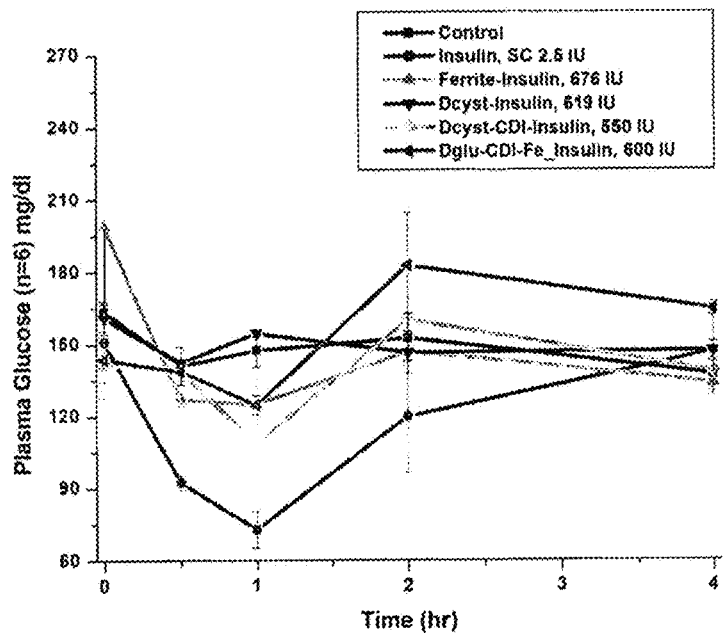
FIG. 8: Oral in vivo activity of non-working formulation compared with subcutaneous insulin and control. The absence of ferrite nanoparticles or d-cystine or CDI is giving negative impact to the decrease in blood glucose.
Figure 9:
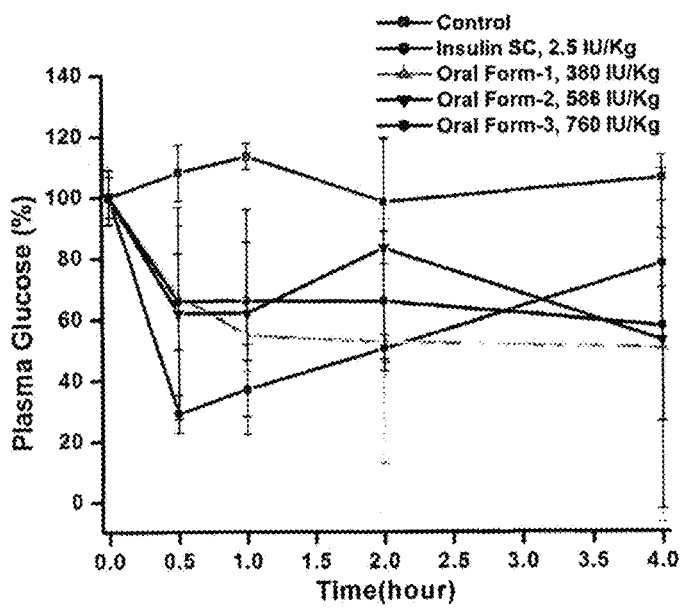
FIG. 9: Oral in vivo activity of formulation compared with subcutaneous insulin. Discrete ferrite nanoparticles 3-5 nm (FIG. 5) present in solution aggregated on adding insulin indicated surface hydroxyl groups present on ferrite nanoparticles favored insulin adsorption.
Figure 10:
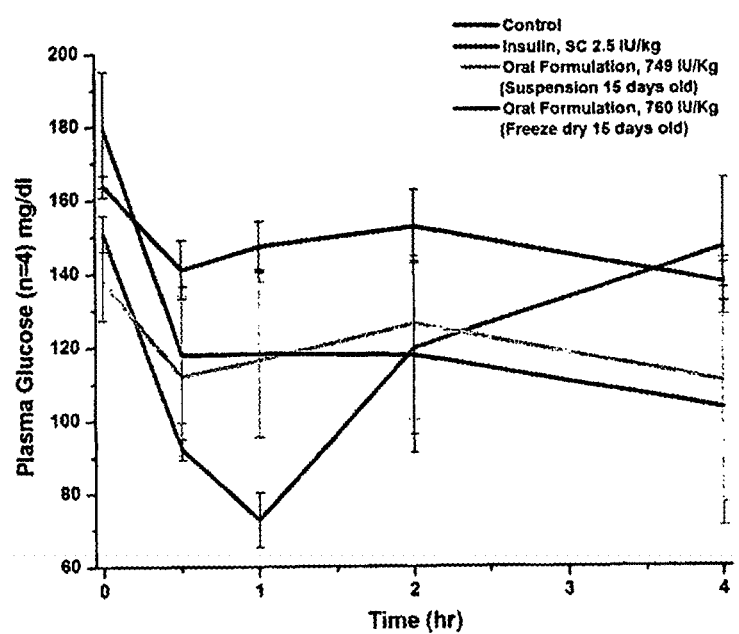
FIG. 10: Oral delivery of 15 days old formulation d-cystine-CDI-Fe-Insulin in suspension state as well as freeze dried formulation is showing decrease in plasma blood glucose as compare to subcutaneous insulin (2.5 IU/Kg) in 4 hr fasted Wistar rats.

In vitro studies in SGF and SIF (FIG. 7) showed 50% and 10% insulin release within 10 minutes respectively denotes the stability of formulation. In vivo studies revealed that oral administration of d-cystine/Insulin/ferrite adduct suspension decreases 46+/−3.6% (n=13) blood glucose level. The decrease in plasma glucose level over a period of 4 hr showed trend with drastic decrease of ~34% within 30 min followed by sustained decline in next 3.5 hr (FIG. 9). While d-glutamine-insulin formulation replacing d-cystine is not able to reduce glucose. As well as formulations without ferrite nanoparticles or d-cystine or CDI is also not able to reduce glucose level (FIG. 8). The lyophilized version of the formulation stored for 15 days was also found to reduce plasma blood glucose level (FIG. 10).

Indeed, the ten times excess ferrite (5.5 mM) present in solution has stabilized the insulin-ferrite aggregates to remain in suspension. During later stage, to form adducts with d-cystine, insulin coated on ferrite nanoparticles exposes it active sites for effective conjugation, although the active sites are not identified here. CDI activator present in reaction mixture also enhances binding of ferrite with proteins and conjugation of protein with d-cystine due to reaction between hydroxyl, carboxyl and amino groups present in the reacting mixture constituents. D-cystine which is very stable to gastric fluids has formed protective shell around the insulin-ferrite aggregates and prevented the degradation of insulin from gastric environment during oral administration.

It is critical to note that, during addition of d-cystine at pH 8 to ferrite-insulin suspension at pH ~1 the pH of the suspension should be maintained at pH 5.5 (isoelectric point of insulin) to maximize nucleation of insulin and to minimize insulin denaturation. From thermodynamic principles, it is understood that the excess surface free energy of nascent nuclei is decreased by interaction with another nucleating species or foreign nuclei present around. Thus, the nascent insulin nucleated in the proximity of ferrite nanoparticles would have favored interaction with d-cystine to form adducts disclosed in the present invention.

The invention claimed is:

1. An orally administrable pharmaceutical preparation comprising a protein loaded on metal oxide nanoparticles and an amino acid wherein the protein is adsorbed on the metal oxide nanoparticles; and wherein the amino acid forms an adduct with the protein loaded on metal oxide nanoparticles and thereby the amino acid encapsulates the protein loaded on the metal oxide nanoparticles.

2. The orally administrable pharmaceutical preparation as claimed in claim 1, wherein the protein is selected from the group consisting of insulin, insulin analog, insulin derivative, insulin growth factor, GLP-1, calcitonin, interferon, human growth hormone, glucagon, gonadotropin-releasing hormone, glycoprotein, cytokine, interleukin, vaccine, enzyme, hormone analog, an antibody, a Fab Fragment, trypsin, enfuvertide, pramlintide acetate or enzyme inhibitors.

3. The orally administrable pharmaceutical preparation as claimed in claim 2, wherein the insulin is selected from the group consisting of porcine insulin, bovine insulin, feline insulin, human insulin, recombinant insulin, lispro insulin, humalog, lantus, levemir, actrapid, novorapid, velosulin, humulin M3, hypurin, insuman, insulatard, mixtard, aspart insulin, glargine insulin, insulin glulisine, isophane insulin, insulin detemir, insulin zinc extended, novolin R, humulin R, humulin R regular U-500, novolin N, Humulin N, ReliOn, afrezza, humulin 70/30, novolin 70/30, novolog 70/30, humulin 50/50, humalog mix 75/25.

4. The orally administrable pharmaceutical preparation as claimed in claim 1, wherein the metal oxide nanoparticles are selected from the group consisting of iron oxide, aluminium hydroxide, magnesium hydroxide, alumina, aluminosilicate, aluminosilicophosphate, silica, zinc oxide, titania, zirconia, tantalum oxide.

5. The orally administrable pharmaceutical preparation as claimed in claim 1, wherein the amino acid is a sulfur containing amino acid.

6. The orally administrable pharmaceutical preparation as claimed in claim 5, wherein the amino acid is d-cystine.

7. The orally administrable pharmaceutical preparation as claimed in claim 1, wherein the amino acid is linked to the protein loaded on metal oxide nanoparticles via carbodiimide.

8. The orally administrable pharmaceutical preparation as claimed in claim 1, wherein adduct of the amino acid with the protein loaded on metal oxide nanoparticles has a size less than 500 nm.

9. The orally administrable pharmaceutical preparation as claimed in claim 1, wherein the amino acid encapsulates the protein loaded on metal oxide nanoparticles at the isoelectric point of the protein.

10. The orally administrable pharmaceutical preparation as claimed in claim 1, wherein said pharmaceutical preparation comprises d-cystine linked with insulin coated a-iron oxide nanoparticles.

11. A process for the production of orally administrable pharmaceutical preparation comprising the steps of:
 a. synthesizing metal oxide nanoparticles by hydrolysis of metal salts and storing the nanoparticles suspension at 0° C. to I 0° C.;
 b. dissolving a protein in an aqueous solution and adjusting the pH of the solution from 7 pH to 2 pH;
 c. adding the protein solution of step (b) to the nanoparticles suspension of step (a) wherein the protein is adsorbed on the metal oxide nanoparticles;
 d. mixing an amino acid solution with a carbodiimide (CDI) solution for 1 minute to 120 minutes and adjusting the pH of the resultant solution to 8 to 9 using an acid;
 e. adding the amino acid-CDI mixture of step (d) to the suspension of step (c), wherein the amino acid forms an adduct with the protein loaded on metal oxide nanoparticles and thereby the amino acid encapsulates the protein loaded on the metal oxide nanoparticles, and maintaining the pH of the solution at the isoelectric point of the protein and storing the resultant solution at 0° C. to 10° C. for 12 hours to 48 hours; and
 f. washing the settled nanoparticles with an aqueous solution to obtain the orally administrable pharmaceutical preparation containing protein.

12. The process as claimed in claim 11, wherein the amino acid solution is prepared by dissolving the amino acid in a basic solution.

13. The process as claimed in claim 12, wherein the basic solution is 30% ammonium hydroxide in distilled water.

14. The process as claimed in claim 11, wherein the carbodiimide (CDI) solution is prepared by dissolving carbodiimide in the aqueous solution.

15. The process as claimed in claim 11, wherein the metal oxide nanoparticles is α-iron oxide nanoparticles, the protein is insulin, the amino acid is d-cystine and the pH of the pharmaceutical preparation is 5.5.

16. The process as claimed in claim 11, wherein the pharmaceutical preparation prior to administration is suspended in the aqueous solution and metal oxide nanoparticle suspension and the pH is maintained at 1 to 2.5.

17. The process as claimed in claim 11, wherein the aqueous solution is selected from the group consisting of water, distilled water, double distilled water or sterilized water.

18. The orally administrable pharmaceutical preparation as claimed in claim 1, wherein the protein comprises insulin, wherein the metal oxide nanoparticles comprise iron oxide, wherein said pharmaceutical preparation comprises d-cystine linked with insulin coated α-iron oxide nanoparticles.

* * * * *